United States Patent [19]
Fischer et al.

[11] Patent Number: 5,703,360
[45] Date of Patent: Dec. 30, 1997

[54] AUTOMATED CALIBRANT SYSTEM FOR USE IN A LIQUID SEPARATION/MASS SPECTROMETRY APPARATUS

[75] Inventors: Steven M. Fischer, Hayward; Robert G. Nordman, Palo Alto; Mark H. Werlich, Santa Clara, all of Calif.

[73] Assignee: Hewlett-Packard Company, Palo Alto, Calif.

[21] Appl. No.: 706,390

[22] Filed: Aug. 30, 1996

[51] Int. Cl.⁶ .................................................... H01J 49/04
[52] U.S. Cl. ........................................ 250/288; 250/252.1
[58] Field of Search ............................. 250/288, 288 A, 250/252.1, 281, 282

[56] References Cited

U.S. PATENT DOCUMENTS

| | | |
|---|---|---|
| 2,822,475 | 2/1958 | Miller . |
| 4,016,421 | 4/1977 | Hull et al. .......................... 250/288 A |
| 4,207,465 | 6/1980 | Favre et al. ........................ 250/288 |
| 4,260,886 | 4/1981 | Grilletto et al. .................... 250/288 |
| 4,495,414 | 1/1985 | Barrie et al. ...................... 250/288 |
| 4,847,493 | 7/1989 | Sodal et al. ....................... 250/288 |
| 4,866,270 | 9/1989 | Hall et al. ........................ 250/282 |
| 4,916,313 | 4/1990 | Hall et al. ........................ 250/288 A |
| 5,175,431 | 12/1992 | Eisele et al. ...................... 250/288 |

FOREIGN PATENT DOCUMENTS

1160821A1  7/1983  U.S.S.R. .

OTHER PUBLICATIONS

Hewlett Packard Operators Manuel, "5985ᴮ LC/MS System," *LC/MS Interface Operators Manual* 05985-90151:i-41 (1980) no month.

Primary Examiner—Kiet T. Nguyen

[57] ABSTRACT

An automated calibrant system is provided for use in a liquid separation/mass spectrometry (LS/MS) apparatus. The calibrant system is pneumatically pressurized to forcibly move a reference liquid from the calibrant system to an ion source. The ion source is in fluid communication with a switching valve and with a mass spectrometer. The switching valve communicates effluent from a liquid separation system to the source when the switching valve is in a first position, and communicates one or more reference liquids from the calibrant system to the source when the switching valve is in a second position. The switching valve, and liquid handling valves in the calibrant system, can be individually activated manually or by automated means to alternate between analytical and calibration modes of operation in the LS/MS apparatus. A method is also provided for calibrating a mass spectrometer in a LS/MS apparatus during processing of a liquid sample by the liquid separation system.

16 Claims, 6 Drawing Sheets

AUTOMATED CALIBRANT SYSTEM FOR USE IN A LIQUID SEPARATION/MASS SPECTROMETRY APPARATUS

TECHNICAL FIELD

The invention relates generally to a liquid separation/mass spectrometry (LS/MS) apparatus. More particularly, the invention relates to an automated calibrant system in an LS/MS apparatus which provides a volume of a reference liquid to the mass spectrometer for use in calibration and/or tuning of the mass spectrometer.

BACKGROUND OF THE INVENTION

Mass spectrometry is used for quantitative elemental analysis, identification of chemical structures and the determination of molecular weight and/or composition of mixtures. Mass spectrometry can be used to ascertain the molecular weights of molecules or the identity of components of a sample based on the detection of a fragmentation pattern of ions produced when the material is ionized.

Mass spectrometry involves the formation of ions from analyte molecules, the separation of the various ions according to their mass-to-charge ratio (m/z), and the subsequent generation of a mass spectrum obtained from the separated ions as a result of their having passed through an electric field, a magnetic field or a combination thereof.

The combination of mass spectrometry with liquid chromatography or capillary electrophoresis separation techniques provides a powerful analytical approach to identifying molecular species in a liquid sample. Such systems have the ability to separate solutions containing mixtures of organic or inorganic molecules into liquid fraction effluents containing discrete compounds and can be used in the analysis of a wide variety of liquid samples. In order to analyze the effluents with a mass spectrometer which operates in a high vacuum system, the liquid effluent is generally prepared for ionization and analysis using atmospheric pressure ionization sources such as electrospray and Atmospheric Pressure Chemical Ionization (APCI) sources. When interfaced to mass spectrometers, electrospray and APCI ionization sources can be used to produce ions from continuously flowing liquid samples to provide on-line detection for liquid separation systems.

Mass spectrometer instruments used in LS/MS systems must be consistently tuned and calibrated in order to preserve detection performance. Tuning and calibration operations entail the use of reference liquid standards which are ionized and then analyzed by the mass spectrometer to provide a signal used to calibrate the axis of the mass filter, and/or tune and assess the operability of various electronic components of the mass spectrometer.

In gas chromatography/mass spectrometer (GC/MS) systems, calibration of the mass spectrometer can be conducted by opening a valve to allow vapor from a sample to permeate the vacuum chamber. By ionizing the vapor, the mass spectrometer can be readily tuned. After adjustment, the valve is simply shut, and the instrument is available for analytical operation. By contrast, ionization in LS/MS systems via electrospray or APCI occurs external to the vacuum system. Particularly, electrospray and APCI ion sources produce ionized molecules from a liquid sample at or near atmospheric pressure within an ion source, and deliver the ionized molecules into vacuum where they are accelerated and focused into a mass analyzer. Such ionization involves significantly more complex liquid handling and valving configurations than internal ionization in GC/MS systems.

Accordingly, calibration or tuning operations in such LS/MS systems are consequently much more complex than in GC/MS systems.

Currently, tuning or calibration operations performed on mass spectrometers in an LS/MS system are conducted in one of several ways. One approach entails the manual injection of a reference liquid into the mass spectrometer. The reference liquid is generally infused by a syringe pump to provide a quantity of calibrant to the ion source at a flow rate sufficient to provide an adequate signal for tuning of the device. Other methods involve infusion of reference liquids into the mass spectrometer, either by an associated liquid separation system or a pneumatically driven liquid injector.

The emphasis in such prior calibration methods has been on the infusion of a reference liquid into the ion source at correct flow rate so as to provide an adequate tuning signal. Further, prior methods involve manual operations, where an external source of reference liquid must be interfaced to the mass spectrometer after disconnecting the liquid separation system from the mass spectrometer. None of these prior calibration and/or tuning operations can be readily conducted using automated machinery. In addition, prior calibration methods involve significant post operation procedures, such as the manual removal of reference liquid carry-over from the liquid handling, valving and ion source. This is particularly important in those prior systems where the liquid sample analyte and the reference liquid are introduced into the ion source by the same flow apparatus.

SUMMARY OF THE INVENTION

The invention provides a liquid separation/mass spectrometer (LS/MS) analytical apparatus, wherein the ion source of the mass spectrometer is in fluid communication with a switching valve that communicates effluent from a liquid separation system to the source when the switching valve is in a first position corresponding to the analytical mode of operation, and communicates one or more reference liquids from a calibrant system to the ion source when the switching valve is in a second position corresponding to the calibration mode of operation. Actuation of the switching valve can be automated to allow change between analytical and calibration modes of operation in the mass spectrometer without the need for manual technician manipulation.

The provision of an automated calibrant system in the LS/MS analytical apparatus represents a substantial departure from conventional methods of tuning or calibrating mass spectrometers in LS/MS systems which involve ionization of the liquid samples external to the vacuum. Such conventional methods generally require several manual operations to (1) disconnect the liquid separation system from the mass spectrometer, (2) interface an external source of reference liquid to the mass spectrometer, (3) infuse the reference liquid into the ion source at a sufficient flow rate for calibration operations, (4) remove residual or carryover reference liquid from the system, and (5) reconnect the liquid separation system to the mass spectrometer.

In one aspect of the invention, the automated calibrant system allows tuning and/or calibration of the mass spectrometer in a LS/MS system using the calibrant system at the same time that the liquid separation system is being used to separate a sample, equilibrate a solvent composition, or purge (e.g., flush) a separation column. In particular, the switching valve is configured to provide fluid communication between the liquid separation system and a means to contain or dispose of waste liquids when the valve is actuated to the second position. Thus, actuating the switching valve to the second position simultaneously allows the communication of reference liquid from the calibrant system to the mass spectrometer for calibration, and the uninterrupted flow of liquid from the liquid separation system to preserve separation efficiency and equilibration or equilibrium in that system.

In another aspect of the invention, the automated calibrant system includes a pressurized source of reference liquid as well as liquid handling conduits and valving which allow the calibrant system, liquid handling conduits and switching valve to be purged clear of any residual or carryover reference liquid after calibration of the mass spectrometer. The pressurized source, liquid handling conduits, valving, and combinations thereof, can be used to regulate the reference liquid delivery rates from the calibrant system to the ion source. Actuation of the valving and the switching valve can be automated to provide automatic operation for calibration and/or tuning of the mass spectrometer.

In yet a further aspect of the invention, the automated calibrant system is provided with two or more reservoirs containing different reference liquids. The calibrant system can be used to supply one or more reference liquids to the ion source either individually or sequentially to perform various tuning or calibration operations, or to provide a plurality of reference liquids to the ion source simultaneously for informative chemical reactions which provide structural and molecular information used in tuning and/or calibrating the mass spectrometer.

DETAILED DESCRIPTION OF THE INVENTION

Before the invention is described in detail, it is to be understood that this invention is not limited to the particular component parts of the devices described or process steps of the methods described as such devices and methods may vary. It is also to be understood that the terminology used herein is for purposes of describing particular embodiments only, and is not intended to be limiting. It must be noted that, as used in the specification and the appended claims, the singular forms "a," "an" and "the" include plural referents unless the context clearly dictates otherwise. Thus, for example, reference to "a calibrant" includes two or more calibrants, reference to "a delivery means" encompasses two or more such means, and the like.

In this specification and in the claims which follow, reference will be made to a number of terms which shall be defined to have the following meanings:

As used herein, a "calibrant," "standard," or "reference liquid" is an aqueous composition comprising a known concentration of an analyte. As is well known in the art, calibrants are used to establish the response of a mass spectrometer measurement system to an analyte. As such, a calibrant is typically any of the various types of standards used to indicate whether an analytical instrument is working within prescribed limits, such that adjustments may be made to the analytical measurement system to correct for deviation from prescribed limits.

"Calibrating" a mass spectrometer is intended to mean determining, by exposing the spectrometer to a calibrant, standard, or reference liquid, the change in the mass spectrum associated with a known concentration of analytes in the standard. By comparing the change in mass spectral read-out with the expected, theoretical value, deviations in the mass spectral read-out can be detected and either compensated for, or rectified by, calibration and/or tuning of various components of the mass spectrometer instrument. The sensitivity of a mass spectrometer can be fine tuned by adjusting electrostatic and dynamic focusing elements. The peak width and peak shape are effected by adjustments in electronics associated with the mass filter and adjustment of the ion energy.

Figure 1:
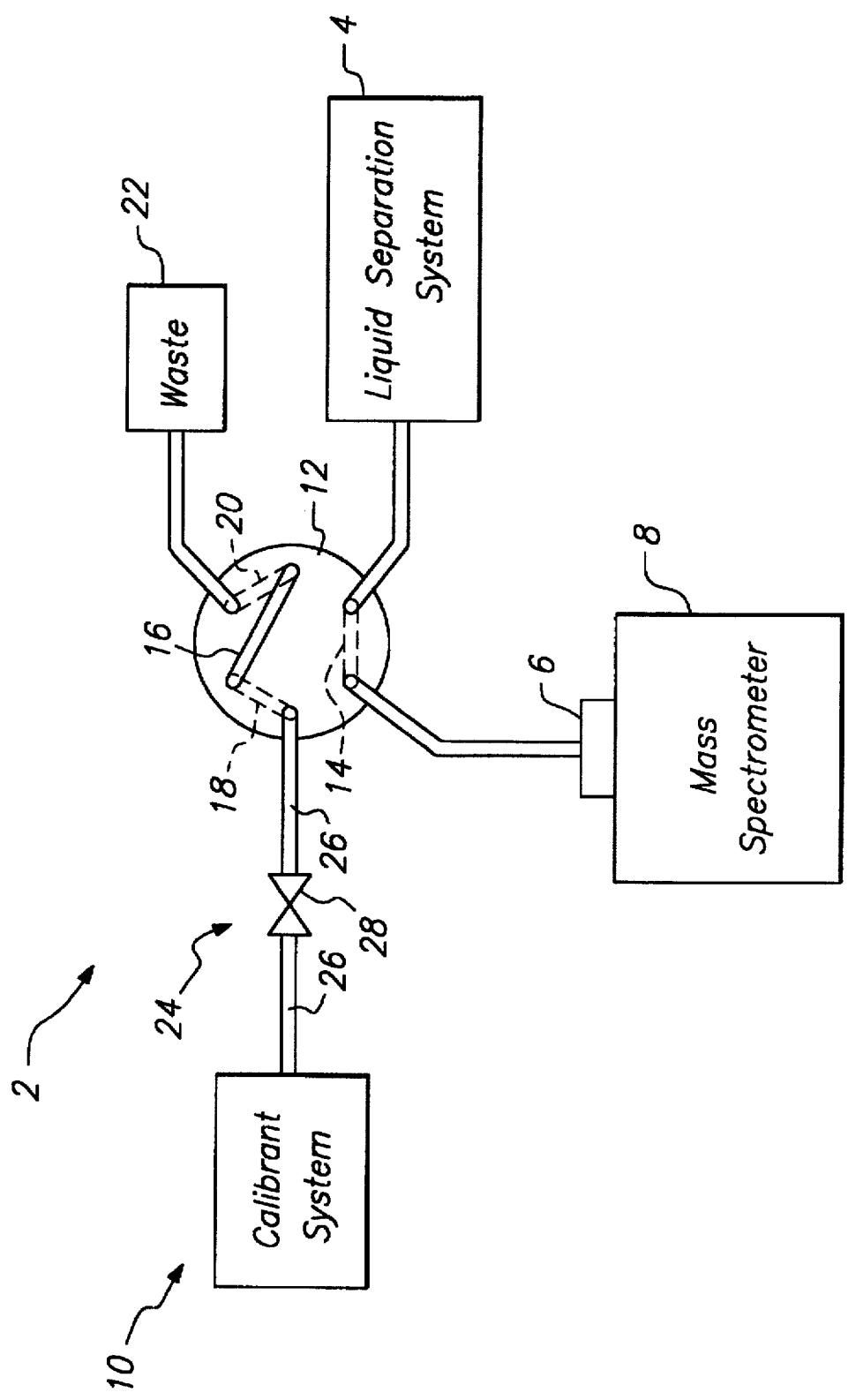
FIG. 1 is a representation of a liquid separation/mass spectrometry (LS/MS) apparatus having a calibrant system in divertable communication with the mass spectrometer during the analytical mode of operation of the LS/MS system.
Figure 2:
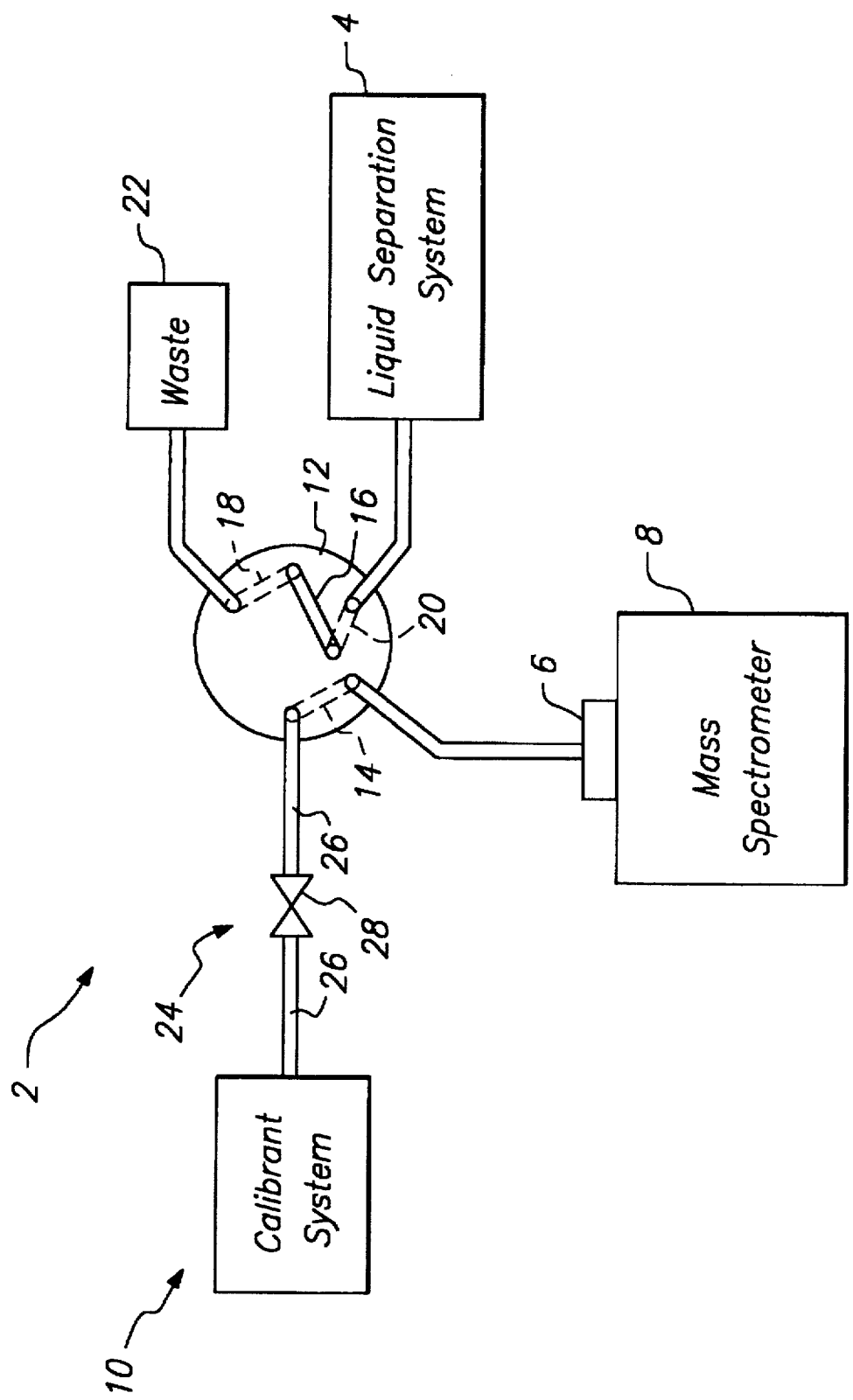
FIG. 2 is a representation of the LS/MS analysis system of FIG. 1 wherein the calibrant system is in divertable communication with the mass spectrometer during the calibration of the LS/MS system.

In one embodiment of the invention, a calibrant system is provided in a liquid separation/mass spectrometry (LS/MS) apparatus. The calibrant system is used for tuning or calibrating the mass spectrometer. In particular, the calibrant system can be used in procedures such as basic calibration of the axis of the mass filter, and/or tuning and assessment of the operability of various electronic components of the mass spectrometer. Referring to FIGS. 1 and 2, one such LS/MS apparatus is generally indicated at 2. The apparatus includes a liquid separation system 4, an ion source 6, a mass spectrometer 8, a calibrant system 10, and, optionally, a means to contain or dispose of liquid waste, generally indicated at 22. The LS/MS apparatus further includes a switching valve 12 which is in fluid communication with the liquid separation system 4 and the calibrant system 10. The switching valve 12 is also in fluid communication with the ion source 6, and allows switchable communication between the ion source and either the liquid separation system 4 or the calibrant system 10.

The mass spectrometer 8 is capable of providing a mass spectrum to permit reliable identification and quantification of sample analytes separated by the liquid separation system 4. Suitable mass spectrometers used herein include quadrupole or other multi-pole mass filters, ion trap detectors, magnetic or electric sector detectors, time-of-flight or ion cyclotron resonance mass analyzers, as well as tandem arrangements such as MS/MS devices.

The liquid separation system 4 separates component analytes of a sample from each other, which sample analytes emerge from the system in liquid fraction effluents. Effluents from suitable liquid separation systems can be ionized in the ion source for analysis in the mass spectrometer. Liquid separation systems used herein include, but are not limited to, High Performance Liquid Chromatography (HPLC) systems, capillary electrophoresis (CE) and capillary electrochromatography (CEC) separation systems.

The switching valve 12 generally comprises a multi-port valve which is manufactured to provide highly precise switch positioning and internal bores or conduits so as to avoid the introduction of dead volume spaces in the LS/MS apparatus. An exemplary switching valve suitable for use in the apparatus 2 is the RHEODYNE® Model #7750 six position valve (available from Rheodyne, Coatati, Calif.). Referring particularly to FIG. 1, when the switching valve 12 is in a first position corresponding to the analytical mode of operation, effluents from the liquid separation system are communicated to the ion source 6 via the switching valve 12, where the component analytes are ionized to provide charged sample molecules. Specifically, the switching valve 12 comprises a first internal conduit 14 which communicates the liquid separation system with the ion source. The switching valve also comprises an external loop conduit 16 connecting two valve openings of the switching valve and communicating at its opposing ends with second and third internal conduits, indicated at 18 and 20, respectively. When the switching valve 12 is in the first position, the external loop conduit 16, in combination with the second and third conduits 18 and 20, communicates the calibrant system 10 with the means 22 to contain or dispose of liquid waste.

The calibrant system 10 provides a volume of a reference liquid for use in calibration and/or fine tuning of the mass spectrometer 8. The reference liquid can be any standard calibrating solution containing one or more known constituents, and is used as a calibrant in adjusting mass spectrometer operating parameters. Exemplary calibrating solutions include suitable solvent systems containing mixtures of polyethylene glycols (PEGs), CsI clusters, proteins, simple organic compounds, inorganic salts, and/or mixtures thereof. Other calibrating solutions, typically used with electrospray ionization sources, include simple peptide mixes such as a combination of valine, trityrosine and hexatyrosine molecules. Such calibrating solutions are well known in the art. Referring now to FIG. 2, when the switching valve 12 is in a second position corresponding to the calibration mode of operation, the first conduit 14 communicates the calibrant system 10 with the ion source 6 such that the reference liquid can be directed to the ion source. The reference liquid is generally delivered to the ion source at a flow rate of about 25 to about 250 µL/min, and a typical calibration generally takes about 10 minutes. The ion source ionizes the reference liquid to provide charged reference liquid molecules. As described in detail below, when the switching valve 12 is in the second position, the liquid separation system is communicated to the means 22 to dispose or contain waste, thereby providing an uninterrupted flow of effluent from the liquid separation system to provide a continuous separation of the liquid sample.

Calibration generally involves (1) obtaining a mass spectrum of the ionized reference liquid molecules from the mass spectrometer 8, (2) calculating from the mass spectrum a composition value for the analyte in the reference liquid, and (3) comparing the calculated and theoretical composition value with the known concentration of analyte in the reference liquid. By so doing, the mass spectrometer 8 can be fine tuned to optimize sensitivity by adjusting electrostatic and dynamic focussing elements such as the repeller, ion focus and entrance lens. In addition, mass axis values and peak widths can be calibrated using the information provided by the mass spectrum of the reference liquid. After the calibration and tuning operations are completed, carryover or residual reference liquid calibrant is cleared from the calibrant system, liquid handling lines, and the internal conduit 14 of the switching valve, and the switching valve 12 is then switched back to the first position to resume or initiate analytical LS/MS operations.

Referring still to FIG. 2, when the switching valve 12 is changed from the first to the second position (from the analytical mode to the calibration mode), the external loop conduit 16 communicates the liquid separation system 4 with the means 22 to contain or dispose of liquid waste. In this manner, adjusting the switching valve to the second position allows effluent emerging from the liquid separation system to be diverted from the ion source 6 and pass to waste, avoiding interruption in the flow of effluent from the separation system during calibration of the mass spectrometer. This feature enables calibration of the mass spectrometer using the calibrant system concurrently with the use of the liquid separation system to separate a sample, equilibrate a solvent composition, or purge and/or flush a separation column. By avoiding interruption of the flow of effluent, the separation efficiency and the equilibration or equilibrium of the liquid separation system are maintained. Further, the system may be repeatedly calibrated during separation of a sample by the liquid separation system by switching between a first position corresponding to the analytical mode of .operation, and second position corresponding to the calibration mode of operation.

In the apparatus depicted in FIGS. 1 and 2, the calibrant system 10 comprises a pressurized source of reference liquid which is in fluid communication with the switching valve 12 by way of a delivery means, generally indicated at 24. The delivery means 24 is comprised of any suitable conduit or fluid line 26 capable of conducting reference liquid from the calibrant system 10 to the ion source 6 when the switching valve 12 is actuated to its second position. Optionally, a delivery means valve 28 may be interposed between the calibrant system 10 and the switching valve 12 such that flow of reference liquid to the switching valve can be diverted or blocked by actuation of the delivery means valve 28 to conserve the reference liquid. When a calibration is carried out, actuation of the delivery means valve 28 and actuation of the switching valve 12 to the second position allows flow of the reference fluid, which is forcibly directed from the calibrant system 10 by, for example, pneumatic pressure, through the delivery means 24 to the ion source 6.

Referring particularly to FIG. 2, the delivery means valve 28 optionally comprises a multi-port valve, for example a two- or three-way valve, which can be actuated to a position that blocks the flow of reference liquid from the calibrant system 10, while allowing gas, for example nitrogen, from the pressurized source to pass through the delivery means fluid line 26 and the conduit 14 in the switching valve 12. After calibration and/or tuning of the mass spectrometer has been carried out, the calibrant system 10, the delivery means 24 and the switching valve 12 can thus be purged to remove any carryover or residual reference liquid from the lines prior to resuming or initiating analytical operation of the LS/MS apparatus. This purging operation can be easily carried out with each calibration, and is readily automated. The use of the three-way valve to clear the reference liquid from the system keeps the calibrant system fluid lines clear, avoiding the possible crystallization of solvents and concomitant blockage of those lines.

The rate of flow of reference liquid from the calibrant system 10 can be readily adjusted by regulation of the pressurizing source. Specifically, the amount of pressure supplied by the pressurizing source can be adjusted to accommodate delivery of reference liquids of different viscosities, wherein the pressurizing source is generally operated in the range of 10 psi. In addition, the rate of flow of reference liquid to the ion source can be regulated and/or adjusted by selecting a delivery means conduit 26 with an internal aperture sufficient to control or restrict the pressurized flow of the liquid therethrough. Alternatively, the flow rate can be regulated by the addition of an in-line flow restrictor in the delivery means 24 which is interposed between the Calibrant system 10 and the switching valve 12. In other alternative configurations, the delivery means valve 28 itself can be used to provide a flow restriction sufficient to regulate and/or adjust the pressurized flow of the reference liquid therethrough. The use of a regulatable motive force and selected flow restriction means allows one to custom tailor the flow rate of the reference liquid through the calibrant system to provide adequate signal for tuning and/or calibrating the mass spectrometer. Acute control over the flow rate of the reference liquid also allows one to preserve the LS/MS system robustness by minimizing excessive delivery of the reference liquid which could overload or contaminate the ion source as well as waste expensive reference liquids.

Figure 3:
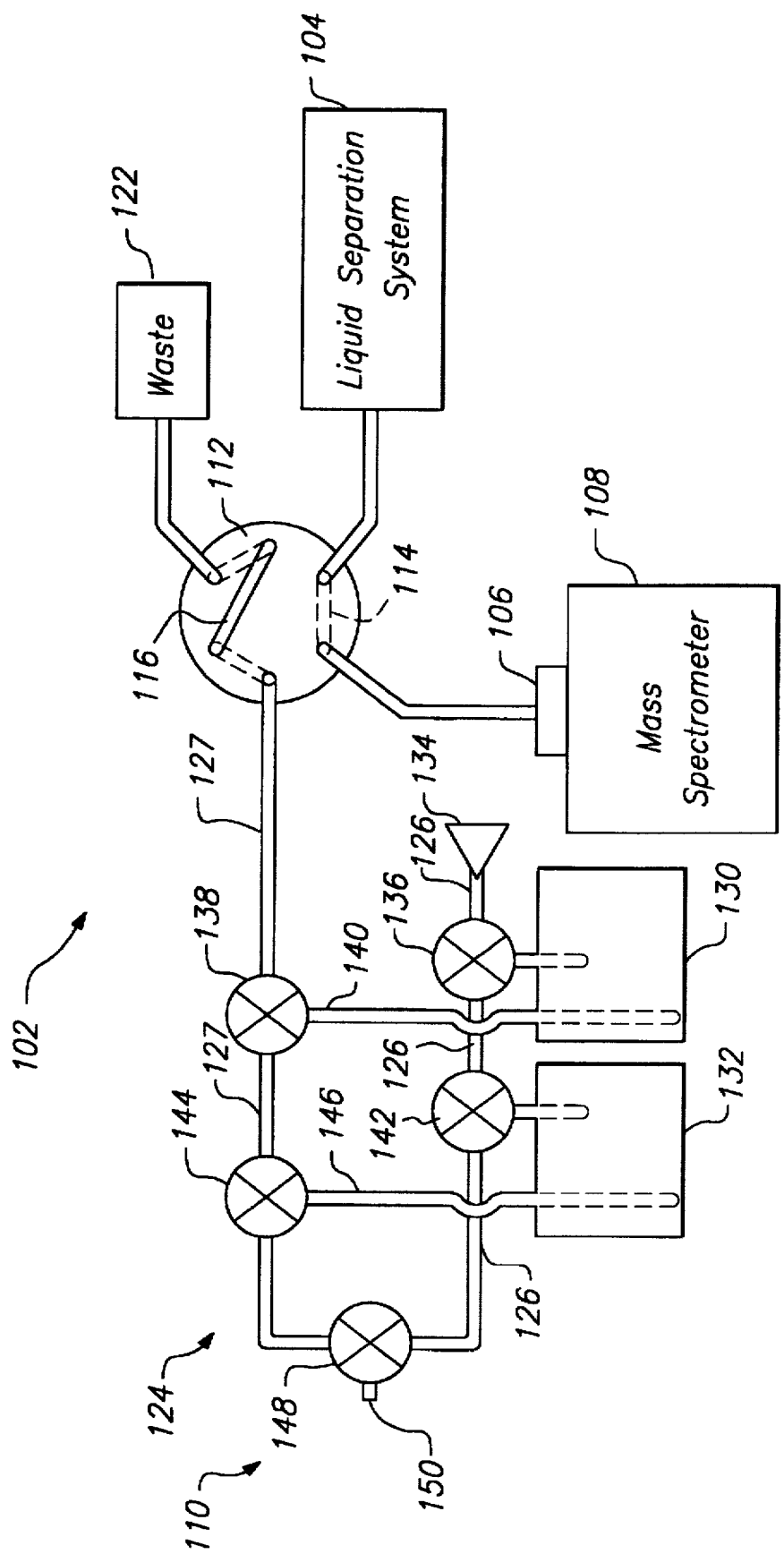
FIG. 3 is a representation of an alternative embodiment of a LS/MS system having a calibrant system with a plurality of reference liquid reservoirs. The calibrant system is in divertable communication with the mass spectrometer during an analytical mode of operation.
Figure 4:
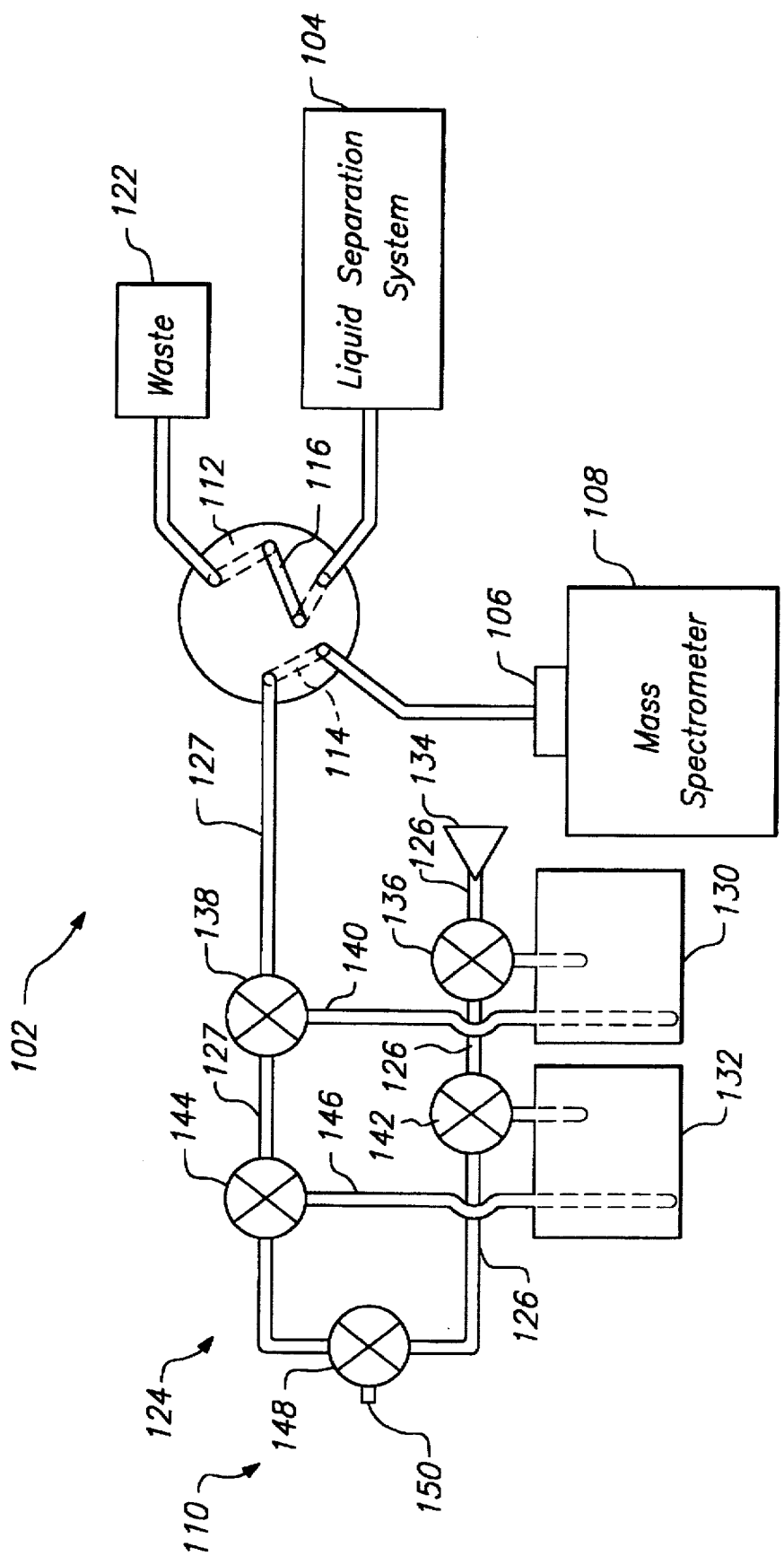
FIG. 4 is a representation of the LS/MS analysis system of FIG. 3 wherein the calibrant system is in divertable communication with the mass spectrometer during calibration.

Referring now to FIGS. 3 and 4, another embodiment of a calibrant system is provided in a liquid separation/mass spectrometry (LS/MS) apparatus. Specifically, a LS/MS apparatus is generally indicated at 102. The apparatus includes a liquid separation system 104, an ion source 106, a mass spectrometer 108, a calibrant system, generally indicated at 110, and, optionally, a means 122 to contain or dispose of liquid waste. The apparatus also includes a switching valve 112 which is in fluid communication with the liquid separation system 104 and the calibrant system 110. The switching valve 112 is also in fluid communication with the ion source 116, and allows switchable communication between the ion source and either the liquid separation system 104 or the calibrant system 110.

As described earlier in connection with the other embodiments of the invention, the switching valve 112 generally comprises a multi-port valve that alternatively enables fluid communication between the liquid separation system 104 and the ion source 106, when adjusted to the first position (i.e., the analytical mode) as shown in FIG. 3, or between the calibrant system 110 and the ion source when adjusted to the second position (i.e., the calibration mode), as shown in FIG. 4. Fluid communication between the various elements of the LS/MS apparatus 102 through the switching valve is provided by a series of internal conduits in the switching valve and an external loop conduit 116 communicating two valve openings, as also described above. In particular, the external loop conduit 116 allows communication between the liquid separation system 104 and the means 122 to contain or dispose of waste when the switching valve 112 is actuated to the second position.

The calibrant system 110 comprises multiple reservoirs for containing a plurality of volumes of the same or different reference liquids. This configuration allows selection between various reference liquids for different tuning and/or calibration operations which can be run individually or sequentially. Additionally, the multiple reservoir calibrant system allows one or more reference liquids to be applied simultaneously to the ion source for informative chemical reactions which aid in structural and/or molecular elucidations in calibration of the mass spectrometer. In one embodiment, the calibrant system 10 includes a first reservoir 130 containing a first reference liquid, and a second reservoir 132 containing a second reference liquid. The first and second reference liquids are communicated to the switching valve 112 via delivery means, generally indicated at 124. A motive means 134 is provided which is used to deliver the first and second reference liquids from the calibrant system 110 to the ion source 106 via the switching valve 112. The motive means may be of an impulse type, providing transfer of a quantal amount of a reference liquid to the ion source, or a continuous flow type which delivers a dynamic amount of the reference liquids to the ion source. In one particular embodiment, the motive means 134 is a pressurized pneumatic system, such as a source of pressurized gas.

The delivery means 124 is comprised of a series of conduits and three-way valves which allow a number of different operations to be conducted with the calibrant system during calibration of the mass spectrometer. In particular, three-way delivery means valves 136 and 138 communicate the first reservoir with the switching valve 112 through the combination of conduits 126, 148, and 147. In like manner, three-way delivery means valves 142 and 144 communicate the second reservoir 132 with the switching valve by way of the combination of conduits 126, 146, and 127. These delivery means components are generally provided in an integrated assembly. By selectively actuating different combinations of the three-way delivery means valves 136, 138, 142, and 144, the calibrant system 110 can be used to either selectively deliver the first and/or second reference liquids to the ion source, or the valves can be used to selectively block or divert the flow of the first and/or second reference liquids from the first and second reservoirs.

Referring now to FIG. 4 wherein the switching valve 112 is actuated to its second position corresponding to the calibration mode, the first reference liquid contained within the first reservoir 130 can be communicated to the ion source 106 during calibration and/or tuning of the mass spectrometer as follows. The first reservoir is pressurized by actuation of the delivery means valve 136 to an on position which allows passage of gas from the motive means 134, through the conduit 126 and into the reservoir. Delivery of the first reference liquid is effected by actuation of both valves 136 and 138 to their respective on positions. This supplies sufficient gas pressure from the motive means to forcibly direct the reference liquid from the first reservoir 130 through conduit 140 and valve 138 whereupon the first reference liquid passes through the delivery means conduit 127 and the internal conduit 114 of the switching valve 112 to enter the ion source 06 for ionization thereof. The other delivery means valves, 142 and 144 are kept in their respective off positions.

As explained above with respect to the first reference liquid, fluid communication of the second reference liquid contained within the second reservoir 132 to the ion source 106 is carried out as follows. The second reservoir is pressurized by actuating the delivery means valve 142 to its on position, thereby communicating gas pressure from the motive means 134 into the reservoir. Delivery of the second reference liquid is effected by actuating both valves 142 and 144 to their respective on positions. This supplies sufficient gas pressure from the motive means to forcibly direct the reference liquid from the second reservoir 132 through conduit 146 and valve 144, allowing the second reference liquid to flow through the delivery means conduit 127 and the internal conduit 114 of the switching valve 112, which has been actuated to its second position, to enter the ion source 106 for ionization thereof. The other delivery means valves, 136 and 138 are kept in their respective off positions.

After completion of a calibration operation wherein the first and/or second reference liquid has been delivered to the ion source, the delivery means conduits and, particularly, the internal conduit 114 of the switching valve 112, can be pneumatically blown clear to prevent or minimize sample carryover between the reference liquid reservoirs 130 and 132, as well as prevent carryover or contamination of the effluent emerging from the liquid separation system 104 when the switching valve 112 is actuated to its first position to initiate or resume analytical mode operations.

Referring to FIGS. 3 and 4, a purge valve 148 is provided within the delivery means 124 and interposed between the switching valve 112 and the reference liquid reservoirs 130 and 132. Referring particularly to FIG. 4, after a calibration operation has been carried out using the first and/or second reference liquids, the delivery means valves 136, 138, 142, and 144 can be actuated to their respective off positions, and the purge valve actuated to an on position. This allows passage of gas from the motive means 134 throughout the delivery means conduits 126, 127, and the internal conduit 114 of the switching valve 112 to cleanse residual reference liquids from those conduits prior to actuating the switching valve 112 to its first position to begin or resume analytical operation of the LS/MS apparatus. If desired, the portion of the delivery means conduit between the motive means 134 and the purge valve 148 can be cleaned in isolation from the remainder of the delivery means conduit by opening an outlet port 150 in the purge valve to allow passage of the cleansing gas therethrough.

The rates of flow of the first and second reference liquids from the calibrant system 110 can be regulated by adjusting the magnitude of motive force provided by the motive means 134, as well as by flow restriction means provided by the delivery means conduits, valves, or combinations thereof. In one particular configuration, the flow rate of the reference liquids is regulated by an in-line flow restrictor positioned between the calibrant system 110 and the switching valve 112, for example in delivery means conduit 127. In another configuration, one or both of the delivery means valves 138 and 144 can be used to provide flow restriction sufficient to regulate and/or adjust the pressurized flow of the reference liquids.

Figure 5:
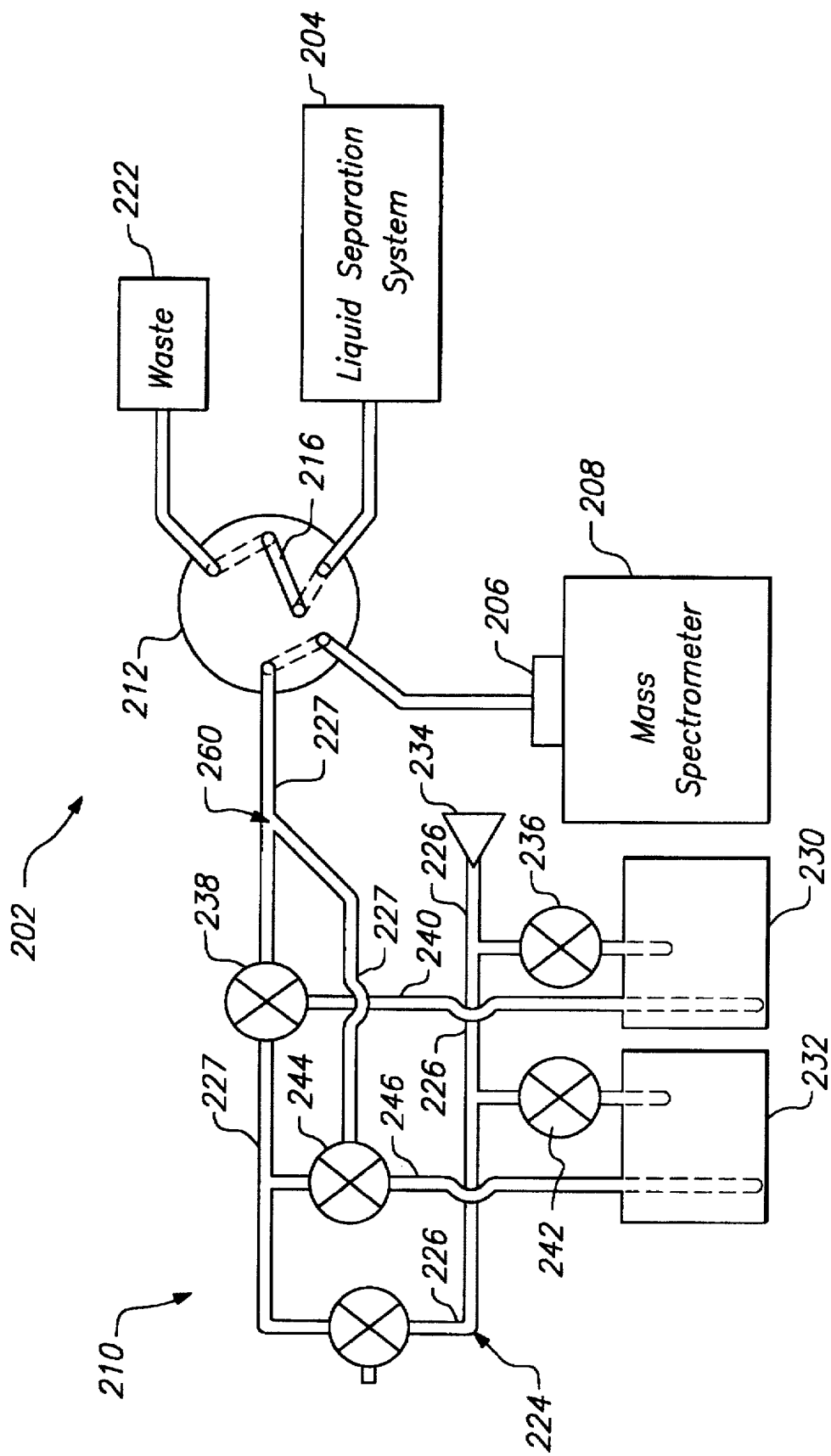
FIG. 5 is a representation of a LS/MS system having a calibrant system with a plurality of reference liquid reservoirs, wherein the calibrant system has a delivery system configured to allow simultaneous delivery of more than one reference liquid to the mass spectrometer during calibration.

Referring now to FIG. 5, an further embodiment of the invention is shown wherein the delivery means is configured to allow simultaneous delivery of two reference liquids to an ion source. Particularly, a LS/MS apparatus 202 includes a liquid separation system 204, an ion source 206, a mass spectrometer 208, a calibrant system, generally indicated at 210, and, optionally, a means 222 to contain or dispose of waste. The apparatus also includes a switching valve 212 which allows communication between the ion source 206 and either the liquid separation system 204 or the calibrant system 210 as described above in the related embodiments of the invention. In FIG. 5, the switching valve 212 is shown in a second position (i.e., the calibration mode).

The calibrant system 210 comprises a first reservoir 230 containing a first reference liquid, and a second reservoir 232 containing a second reference liquid. The reference liquids are communicated to the switching valve 212 through delivery means, generally indicated at 224, by the pneumatic pressure provided by a pneumatic motive means 234. The delivery means 224 is comprised of a series of conduits and valves. In one embodiment, two-way valve 236 and three-way valve 238 communicate the first reservoir 230 with the switching valve 212 through the combination of conduits 226, 240, and 227. Two-way valve 242 and three-way valve 244 communicate the second reservoir 232 with the switching valve through the combination of conduits 226, 246, and 227.

Simultaneous delivery of the first and second reference liquids to the ion source 206 is carried out by actuating the delivery means valves 236, 238, 242, and 244 to each of their respective on positions. In this manner, gas pressure from the motive means 234 is used to forcibly direct both the first and second reference liquids from their respective reservoirs and through the delivery means where they are joined at a mixing tee 260 at a downstream terminus of the conduit 227 to provide a combined stream. The combined stream containing both reference liquids is then communicated to the ion source 106 via an internal conduit 114 of the switching valve 112.

The calibrant systems in the LS/MS devices described herein can be provided with means for actuating the switching valve to allow a reference liquid or an alternative liquid sample to reach the ion source instead of the liquid effluent emerging from the liquid separation system. Accordingly, these calibrant systems can be used in Flow-Injection Analysis of liquid samples. Further, such LS/MS devices can be provided with custom calibrant systems containing a source of one or more reference liquids that are supported by complementary macro tuning or calibration codes which effect automated calibration of the mass spectrometers at prescribed times or intervals.

For example, in the LS/MS apparatus 2 depicted in FIGS. 1 and 2, the switching valve 12 and the optional delivery means valve 28 can be electrically or pneumatically actuated by a signal provided by the LS/MS apparatus to alternate between calibration and analytical modes of operation. In the LS/MS apparatus 102 depicted in FIGS. 3 and 4, the switching valve 112, the purge valve 148, and the three-way delivery means valves 136, 138, 142, and 144 can each be individually actuated by way of electrical or pneumatic means to provide either calibration or analytical operations. Likewise, in the LS/MS apparatus 202 shown in FIG. 5, the switching valve 212, and the delivery means valves 236, 238, 242, and 244 can be automatically actuated for analytical or calibration operations. Actuation of the above valves can be controlled by a computer program which is designed to operate with particular reference liquids. As will be appreciated by one of ordinary skill in the art after reading this specification, such computer programs can be readily changed to accommodate use of different reference liquids in the calibrant system.

Figure 6:
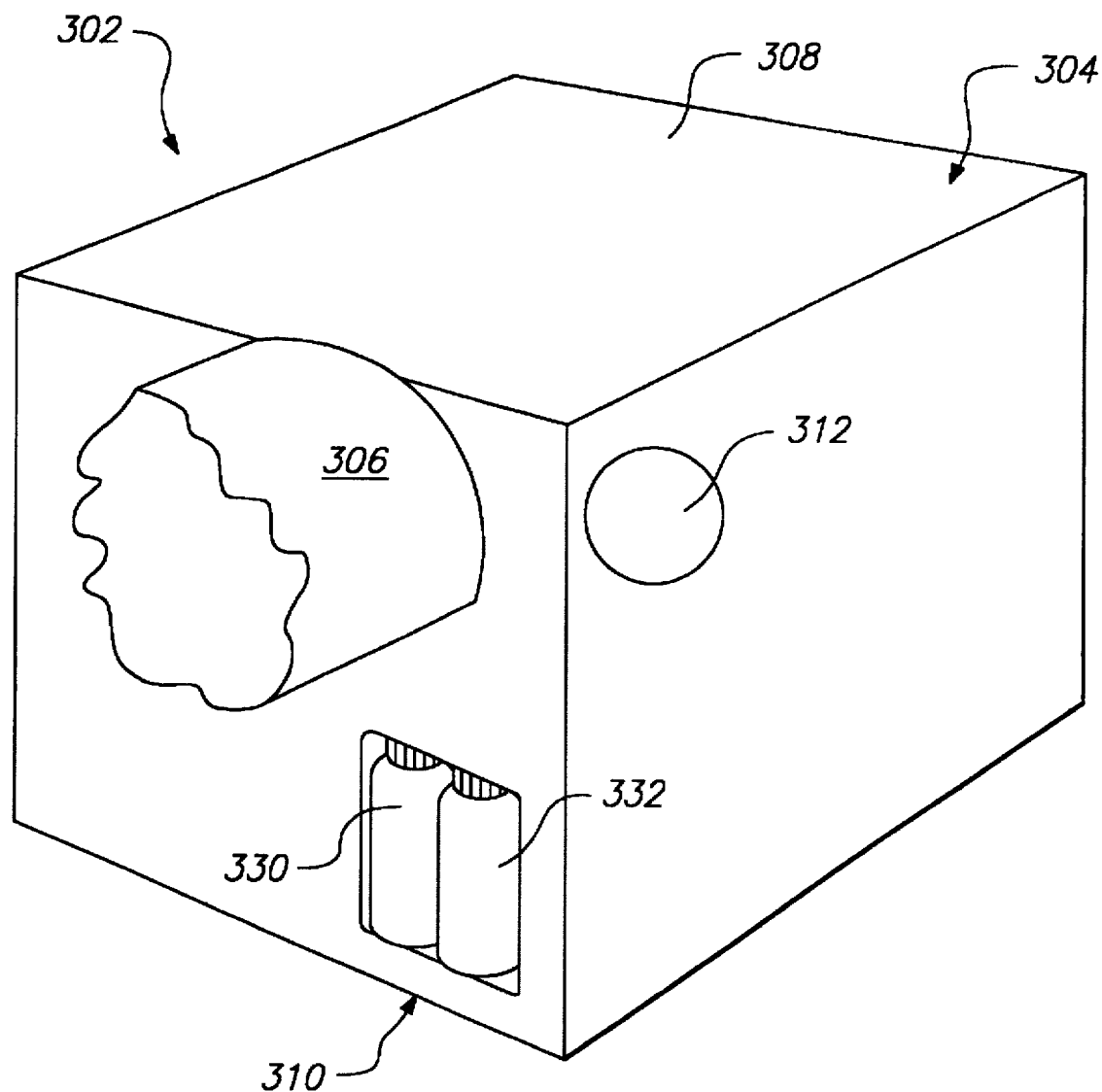
FIG. 6 is a pictorial representation of an embodiment of a LS/MS system having a calibrant system and a mass spectrometer that are contained within a single housing.

The LS/MS devices depicted in FIGS. 1–5 can be provided in an apparatus configuration where the calibrant systems and delivery means are contained within the same housing as the mass spectrometer to provide an internal calibrant system in a LS/MS apparatus. Referring to FIG. 6, a mass spectrometer apparatus having an internal calibrant system is generally indicated at 302. The apparatus 302 includes an ion source 306, a mass spectrometer 308 and an internally-arranged calibrant system 310, wherein the calibrant system along with any delivery means conduits and/or valves, and the mass spectrometer are contained within a single housing, generally indicated at 304. As described above with respect to the LS/MS apparatuses 2 and 102, a switching valve 312 that is in fluid communication with the ion source 306 allows alternation between calibration and analytical modes of operation in the mass spectrometer.

In the apparatus depicted in FIG. 6, the calibrant system 310 includes a first reservoir 330 containing a first reference liquid, and a second reservoir 332 containing a second reference liquid, although the calibrant system can include a single reservoir or a multiplicity of reservoirs. The reservoirs can contain general reference liquids that are supplied by the manufacturer and selected to be used in particular calibration and/or tuning operations, or the reservoirs can contain reference liquids expressly made for particular end-use operations.

In operation, the switching valve 312 is in fluid communication with an externally associated liquid separation system and the calibrant system 310. When the switching valve 312 is actuated to a first position corresponding to an analytical mode of operation, the valve communicates effluent from the separation system to the ion source 306. When the switching valve is actuated to a second position corresponding to a calibration mode of operation, the valve communicates the first and/or second reference liquids from the internal calibrant system 310 to the ion source 306.

It is to be understood that while the invention has been described above in conjunction with preferred specific embodiments, the description and examples are intended to illustrate and not limit the scope of the invention, which is defined by the scope of the appended claims.

We claim:

1. A method of calibrating a mass spectrometer in a liquid separation/mass spectrometer apparatus during processing of a liquid sample, wherein the apparatus includes a mass spectrometer, a liquid separation system which processes a liquid sample to yield an effluent, a calibrant system for providing a volume of a pneumatically pressurized reference liquid, an ion source in fluid communication with the mass spectrometer, and a switching valve in fluid communication with the liquid separation system, the calibrant system and the ion source, the switching valve having a first position which provides fluid communication between the liquid separation system and the ion source, and a second position which simultaneously provides fluid communication of the reference liquid from the calibrant system to the ion source and effluent from the liquid separation system to waste, the method comprising:

(a) initiating processing of a liquid sample by the liquid separation system to provide an effluent;

(b) actuating the switching valve to the first position to communicate the effluent from the liquid separation system to the ion source for conversion therein to an ionized aerosol and for delivery therefrom to the mass spectrometer to initiate analysis of the liquid sample;

(c) actuating the switching valve to the second position to communicate the reference liquid from the calibrant system to the ion source for conversion therein to an ionized aerosol and for delivery therefrom to the mass spectrometer while communicating the effluent from the liquid separation system to waste;

(d) obtaining a mass spectrum of the ionized reference liquid molecules from the mass spectrometer; and (e) actuating the switching valve back to the first position to communicate the effluent from the liquid separation system to the mass spectrometer to resume analysis of the liquid sample.

2. A liquid separation/mass spectrometry apparatus comprising:

(a) a liquid separation system for processing a liquid sample to yield an effluent;

(b) a calibrant system having delivery means and a pneumatic pressure source for providing a volume of a pressurized reference liquid to calibrate a mass spectrometer;

(c) an ion source for converting the liquid sample effluent or the reference liquid into an ionized aerosol;

(d) a mass spectrometer for receiving therein from the ion source the ionized aerosol of the liquid sample effluent or the reference liquid four mass spectral analysis; and (e) a switching valve in fluid communication with the liquid separation system, the calibrant system and the ion source, wherein the switching valve has a first position for communicating the liquid sample effluent from the liquid separation system to the ion source and a second position for communicating the reference liquid from the calibrant system to the ion source.

3. The apparatus of claim 2 wherein the switching valve directs said effluent from the liquid separation system to waste when the switching valve is in the second position, such that the effluent continues to flow from the liquid separation system without interruption.

4. The apparatus of claim 2 wherein the calibrant system comprises a first reservoir containing a first reference liquid and a second reservoir containing a second reference liquid.

5. The apparatus of claim 4, wherein the delivery means comprises a plurality of fluid lines and valves connected thereto between the reservoirs and the switching valve, the valves in different combinations cooperating either to (a) selectively deliver the first reference liquid, the second reference liquid, or both, from the calibrant system to the ion source; or to (b) block or divert the flow of the first reference liquid, the second reference liquid; or both, from the calibrant system.

6. The apparatus of claim 5, wherein the delivery means further comprises flow restriction means sufficient to regulate the pressurized flow rate of the reference liquid delivered therethrough from the calibrant system to the ion source.

7. The apparatus of claim 5 wherein the delivery means valves and fluid lines cooperate to block or divert the flow of said first reference liquid, said second reference liquid, or both from the calibrant system and to allow gas to flow from the pneumatic pressure source through the delivery means to the ion source, thereby to purge residual or carryover reference liquid from the delivery means and the liquid separation/mass spectrometery apparatus.

8. The apparatus of claim 2 or 4, wherein the mass spectrometer and the calibrant system are contained within a single housing.

9. The apparatus of claim 2 wherein actuation of the switching valve is automated.

10. The apparatus of claim 2, wherein the delivery means comprises a fluid line and a valve connected thereto between the calibrant system and the switching valve for blocking or diverting the flow of said reference liquid from the calibrant system.

11. The apparatus of claim 10, wherein the delivery means further comprises flow restriction means sufficient to regulate the pressurized flow rate of the reference liquid delivered therethrough from the calibrant system to the ion source.

12. The apparatus of claim 1, wherein the pneumatic pressure source is regulatable.

13. The apparatus of claim 1 or 6, wherein the flow restriction means is comprised of an in-line flow restrictor.

14. The apparatus of claim 1 or 6, wherein the flow restriction means is comprised of a delivery means valve.

15. The apparatus of claim 10, wherein the delivery means valve cooperates with the fluid line to block or divert the flow of said reference liquid from the calibrant system and to allow gas to flow from the pneumatic pressure source through the delivery means to the ion source, thereby to purge residual or carryover reference liquid from the delivery means and the liquid separation/mass spectrometry apparatus.

16. The apparatus of claim 10 or 5, wherein actuation of the switching valve and the delivery means valve is automated.

* * * * *